US009486155B2

(12) United States Patent
Sarkar et al.

(10) Patent No.: US 9,486,155 B2
(45) Date of Patent: Nov. 8, 2016

(54) METHOD AND APPARATUS FOR ATRIAL ARRHYTHMIA EPISODE DETECTION

(71) Applicant: Medtronic, Inc., Minneapolis, MN (US)

(72) Inventors: Shantanu Sarkar, Roseville, MN (US); Daniel L Hansen, Castle Rock, CO (US); Grant A Neitzell, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/695,135

(22) Filed: Apr. 24, 2015

(65) Prior Publication Data

US 2016/0235315 A1    Aug. 18, 2016

Related U.S. Application Data

(60) Provisional application No. 62/117,785, filed on Feb. 18, 2015.

(51) Int. Cl.
*A61B 5/04* (2006.01)
*A61B 5/046* (2006.01)
*A61B 5/0456* (2006.01)
*A61B 5/00* (2006.01)

(52) U.S. Cl.
CPC ........... *A61B 5/046* (2013.01); *A61B 5/04012* (2013.01); *A61B 5/0456* (2013.01); *A61B 5/686* (2013.01)

(58) Field of Classification Search
CPC A61B 5/046; A61B 5/0456; A61B 5/04012; A61B 5/686
See application file for complete search history.

(56) References Cited

U.S. PATENT DOCUMENTS

| | | |
|---|---|---|
| 4,226,245 A | 10/1980 | Bennett |
| 4,374,382 A | 2/1983 | Markowitz |
| 4,721,114 A | 1/1988 | DuFault et al. |
| 5,117,824 A | 6/1992 | Keimel et al. |
| 5,193,535 A | 3/1993 | Bardy et al. |
| 5,292,338 A | 3/1994 | Bardy |
| 5,312,445 A | 5/1994 | Nappholz et al. |
| 5,334,221 A | 8/1994 | Bardy |
| 5,458,623 A | 10/1995 | Lu et al. |

(Continued)

FOREIGN PATENT DOCUMENTS

| | | |
|---|---|---|
| EP | 2572634 | 3/2013 |
| WO | 9809241 | 3/1998 |

(Continued)

OTHER PUBLICATIONS

"P-wave evidence as a method for improving algorithm to detect atrial fibrillation in insertable cardiac monitors", Helmut Purerfellner, MD. FHRS, et al., 2014 Heart Rhythm Society, vol. 11, No. 9, Sep. 2014, pp. 1575-1583.

(Continued)

*Primary Examiner* — George Manuel

(57) ABSTRACT

A method and medical device for determining a P-wave of a cardiac signal that includes sensing the cardiac signal, determining a P-wave sensing window in response to the sensed cardiac signal, the P-wave sensing window having a first portion and a second portion, determining signal characteristics of the sensed cardiac signal within the first portion and within the second portion, comparing the determined signal characteristics, and determining the P-wave in response to the comparing.

30 Claims, 6 Drawing Sheets

(56) References Cited

U.S. PATENT DOCUMENTS

| | | |
|---|---|---|
| 5,545,186 A | 8/1996 | Olson et al. |
| 5,609,157 A | 3/1997 | Panescu et al. |
| 5,609,158 A | 3/1997 | Chan |
| 5,755,739 A | 5/1998 | Sun et al. |
| 5,782,888 A | 7/1998 | Sun et al. |
| 5,817,134 A | 10/1998 | Greenhut et al. |
| 6,067,473 A | 5/2000 | Greeninger et al. |
| 6,393,316 B1 | 5/2002 | Gillberg et al. |
| 6,470,210 B1 | 10/2002 | Chen et al. |
| 6,516,225 B1 | 2/2003 | Florio |
| 6,745,068 B2 | 6/2004 | Koyrakh et al. |
| 6,865,414 B1 | 3/2005 | Levine |
| 6,895,272 B2 | 5/2005 | Seim et al. |
| 6,904,315 B2 | 6/2005 | Panken et al. |
| 6,904,319 B2 | 6/2005 | Seim et al. |
| 6,912,418 B1 | 6/2005 | Florio |
| 6,922,584 B2 | 7/2005 | Wang et al. |
| 6,931,273 B2 | 8/2005 | Groenewegen et al. |
| 7,031,765 B2 | 4/2006 | Ritscher et al. |
| 7,062,315 B2 | 6/2006 | Koyrakh et al. |
| 7,139,604 B1 | 11/2006 | Mouchawar et al. |
| 7,184,815 B2 | 2/2007 | Kim et al. |
| 7,187,965 B2 | 3/2007 | Bischoff et al. |
| 7,242,978 B2 | 7/2007 | Cao et al. |
| 7,308,308 B1 | 12/2007 | Xi et al. |
| 7,412,282 B2 | 8/2008 | Houben |
| 7,509,160 B2 | 3/2009 | Bischoff et al. |
| 7,515,956 B2 | 4/2009 | Thompson |
| 7,532,928 B2 | 5/2009 | Lang |
| 7,537,569 B2 | 5/2009 | Sarkar et al. |
| 7,561,911 B2 | 7/2009 | Cao et al. |
| 7,570,990 B2 | 8/2009 | Faber et al. |
| 7,580,748 B2 | 8/2009 | Garner et al. |
| 7,593,766 B2 | 9/2009 | Faber et al. |
| 7,596,405 B2 | 9/2009 | Kurzweil et al. |
| 7,623,911 B2 | 11/2009 | Sarkar et al. |
| 7,627,368 B2 | 12/2009 | Houben et al. |
| 7,640,054 B2 | 12/2009 | Koyrakh et al. |
| 7,657,305 B2 | 2/2010 | Nigam |
| 7,657,307 B2 | 2/2010 | Van Dam et al. |
| 7,706,869 B2 | 4/2010 | Cao et al. |
| 7,729,754 B2 | 6/2010 | Cao et al. |
| 7,826,893 B2 | 11/2010 | Cao et al. |
| 7,983,742 B2 | 7/2011 | Starc |
| 7,996,070 B2 | 8/2011 | van Dam et al. |
| 8,000,778 B2 | 8/2011 | Seim et al. |
| 8,064,998 B2 | 11/2011 | Good et al. |
| 8,195,280 B2 | 6/2012 | Van Dam et al. |
| 8,233,980 B2 * | 7/2012 | Pei ................................. 607/9 |
| 8,265,753 B2 | 9/2012 | Higham et al. |
| 8,280,510 B2 | 10/2012 | Dyjach et al. |
| 8,285,377 B2 | 10/2012 | Rosenberg et al. |
| 8,412,316 B2 | 4/2013 | Seim et al. |
| 8,428,697 B2 | 4/2013 | Zhang et al. |
| 8,428,705 B2 | 4/2013 | Kurzweil et al. |
| 8,521,268 B2 | 8/2013 | Zhang et al. |
| 8,548,573 B2 | 10/2013 | Keefe |
| 8,560,058 B2 | 10/2013 | Babaeizadeh et al. |
| 8,588,895 B2 | 11/2013 | Sanghera et al. |
| 8,639,316 B2 | 1/2014 | Sarkar |
| 8,688,469 B2 | 4/2014 | Ziegler et al. |
| 8,718,750 B2 | 5/2014 | Lian et al. |
| 8,923,963 B2 | 12/2014 | Bonner et al. |
| 8,977,350 B2 | 3/2015 | Sarkar et al. |
| 2002/0120206 A1 | 8/2002 | Taha et al. |
| 2003/0023178 A1 | 1/2003 | Bischoff et al. |
| 2005/0065564 A1 | 3/2005 | Seim et al. |
| 2005/0080347 A1 | 4/2005 | Sheth et al. |
| 2006/0074332 A1 | 4/2006 | Bischoff et al. |
| 2006/0079797 A1 | 4/2006 | Bischoff et al. |
| 2006/0079798 A1 | 4/2006 | Bischoff et al. |
| 2006/0106323 A1 | 5/2006 | Bischoff et al. |
| 2006/0167364 A1 | 7/2006 | Houben |
| 2007/0142866 A1 | 6/2007 | Li et al. |
| 2007/0232944 A1 | 10/2007 | Ghanem et al. |
| 2008/0147133 A1 | 6/2008 | Garner |
| 2008/0154318 A1 | 6/2008 | Albus |
| 2009/0216144 A1 * | 8/2009 | Hopenfeld ........... A61B 5/0452 600/521 |
| 2009/0270747 A1 * | 10/2009 | van Dam et al. .............. 600/509 |
| 2010/0030293 A1 | 2/2010 | Sarkar et al. |
| 2010/0114195 A1 | 5/2010 | Burnes et al. |
| 2011/0125206 A1 | 5/2011 | Bornzin et al. |
| 2011/0208079 A1 | 8/2011 | Babaeizadeh et al. |
| 2011/0301661 A1 | 12/2011 | Seim et al. |
| 2011/0319949 A1 | 12/2011 | Bardy |
| 2012/0123232 A1 | 5/2012 | Najarian et al. |
| 2012/0226179 A1 | 9/2012 | Stadler et al. |
| 2012/0238891 A1 | 9/2012 | Sarkar et al. |
| 2012/0238892 A1 | 9/2012 | Sarkar |
| 2013/0172765 A1 | 7/2013 | Stewart |
| 2014/0155722 A1 | 6/2014 | Greenspan et al. |
| 2014/0276154 A1 | 9/2014 | Katra et al. |
| 2014/0350422 A1 | 11/2014 | Stewart |
| 2014/0378851 A1 | 12/2014 | Frei et al. |
| 2015/0073295 A1 | 3/2015 | Gordon et al. |
| 2015/0080752 A1 | 3/2015 | Lian et al. |
| 2015/0105681 A1 | 4/2015 | Bonan et al. |
| 2015/0230722 A1 | 8/2015 | Sarkar et al. |
| 2015/0305642 A1 | 10/2015 | Reinke et al. |
| 2015/0306375 A1 | 10/2015 | Marshall et al. |
| 2015/0306410 A1 | 10/2015 | Marshall et al. |

FOREIGN PATENT DOCUMENTS

| | | |
|---|---|---|
| WO | 01/80042 A1 | 10/2001 |
| WO | 2004108212 A2 | 12/2004 |
| WO | 2012058398 A1 | 5/2012 |

OTHER PUBLICATIONS

Sarkar et al, "Method and Apparatus for Atrial Arrhythmia Episode Detection", U.S. Appl. No. 14/695,156, filed Apr. 24, 2015, 42 pages.

Sarkar et al, "Method and Apparatus for Atrial Arrhythmia Episode Detection", U.S. Appl. No. 14/695,171, filed Apr. 24, 2015, 38 pages.

Sarkar et al, "Method and Apparatus for Atrial Arrhythmia Episode Detection", U.S. Appl. No. 14/695,111, filed Apr. 24, 2015, 51 pages.

Cao et al, "Atrial Arrhythmia Episode Detection in a Cardiac Medical Device ", U.S. Appl. No. 14/604,363, filed Jan. 23, 2015, 46 pages.

Cao et al, "Atrial Arrhythmia Episode Detection in a Cardiac Medical Device ", U.S. Appl. No. 14/604,411, filed Jan. 23, 2015, 48 pages.

Cao et al, "Atrial Arrhythmia Episode Detection in a Cardiac Medical Device ", U.S. Appl. No. 14/604,468, filed Jan. 23, 2015, 46 pages.

Zhang et al, "Method and Apparatus for Beat Acquisition During Template Generation in a Medical Device Having Dual Sensing Vectors", U.S. Appl. No. 14/604,111, filed Jan. 23, 2015, 77 pages.

Zhang et al, "Method and Apparatus for Beat Acquisition During Template Generation in a Medical Device Having Dual Sensing Vectors", U.S. Appl. No. 14/604,260, filed Jan. 23, 2015, 75 pages.

Zhang et al, "Method and Apparatus for Beat Acquisition During Template Generation in a Medical Device Having Dual Sensing Vectors", U.S. Appl. No. 15/002,521, filed Jan. 21, 2015, 80 pages.

Sarkar et al, "Method and Apparatus for Adjusting a Threshold During Atrial Arrhythmia Episode Detection in an Implantable Medical Device", U.S. Appl. No. 14/926,419, filed Oct. 29, 2015, 51 pages.

Sarkar et al, "Method and Apparatus for Identifying Sick Sinus Syndrome", U.S. Appl. No. 14/926,455, filed Oct. 29, 2015, 39 pages.

(56) References Cited

OTHER PUBLICATIONS

Cao et al. "Atrial Arrhythmia Dectection During Interminttent Instances of Ventricular Pacing in a Cardiac Medical Device", U.S. Appl. No. 14/520,798, filed Oct. 22, 2014, 35 pages.

Cao et al. "Atrial Arrhythmia Dectection During Ventricular Pacing in a Cardiac Medical Device", U.S. Appl. No. 14/520,847, filed Oct. 22, 2014, 49 pages.

Cao et al. "Atrial Arrhythmia Episode Dectection in a Cardiac Medical Device", U.S. Appl. No. 14/520,938, filed Oct. 22, 2014, 47 pages.

(PCT/US2016/018383) PCT Notification of Transmittal of the International Search Report and the Written Opinion of the International Searching Authority, Mailed May 23, 2016, 12 pages.

(PCT/US2016/018408) PCT Notification of Transmittal of the International Search Report and the Written Opinion of the International Searching Authority, Mailed May 24, 2016, 13 pages.

Couceri et al., "Detection of Atrial Fibrillation Using Model-Based ECG Analysis", 19th International Conference on Pattern Recognition, Dec. 2008, 5 pages.

(PCT/US2016/018389) PCT Notification of Transmittal of the International Search Report and the Written Opinion of the International Searching Authority, Mailed Jun. 13, 2016, 12 pages.

(PCT/US2016/018496) PCT Notification of Transmittal of the International Search Report and the Written Opinion of the International Searching Authority, Mailed Jun. 13, 2016, 11 pages.

\* cited by examiner

METHOD AND APPARATUS FOR ATRIAL ARRHYTHMIA EPISODE DETECTION

CROSS-REFERENCE TO RELATED APPLICATIONS

This application claims the benefit of U.S. Provisional Application No. 62/117,785, filed on Feb. 18, 2015, incorporated herein by reference in its entirety.

TECHNICAL FIELD

The disclosure relates generally to implantable cardiac medical devices and, in particular, to a method for and apparatus for detecting atrial tachyarrhythmia episodes in an implantable cardiac medical device.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (A-V) node. The A-V node responds by propagating a ventricular depolarization signal through the bundle of His of the ventricular septum and thereafter to the bundle branches and the Purkinje muscle fibers of the right and left ventricles.

Atrial tachyarrhythmia includes the disorganized form of atrial fibrillation and varying degrees of organized atrial tachycardia, including atrial flutter. Atrial fibrillation (AF) occurs because of multiple focal triggers in the atrium or because of changes in the substrate of the atrium causing heterogeneities in conduction through different regions of the atria. The ectopic triggers can originate anywhere in the left or right atrium or pulmonary veins. The AV node will be bombarded by frequent and irregular atrial activations but will only conduct a depolarization signal when the AV node is not refractory. The ventricular cycle lengths will be irregular and will depend on the different states of refractoriness of the AV-node.

In the past, atrial arrhythmias have been largely undertreated due to the perception that these arrhythmias are relatively benign. As more serious consequences of persistent atrial arrhythmias have come to be understood, such as an associated risk of relatively more serious ventricular arrhythmias and stroke, there is a growing interest in monitoring and treating atrial arrhythmias.

Methods for discriminating arrhythmias that are atrial in origin from arrhythmias originating in the ventricles have been developed for use in dual chamber implantable devices wherein both an atrial EGM signal and a ventricular EGM signal are available. Discrimination of arrhythmias can rely on event intervals (PP intervals and RR intervals), event patterns, and EGM morphology. Such methods have been shown to reliably discriminate ventricular arrhythmias from supra-ventricular arrhythmias. In addition, such methods have been developed for use in single chamber implantable devices, subcutaneous implantable devices, and external monitoring devices, where an adequate atrial EGM signal having acceptable signal-to-noise ratio is not always available for use in detecting and discriminating atrial arrhythmias.

Occasionally, false detection of atrial fibrillation may occur in a subcutaneous device during runs of ectopic rhythm with irregular coupling intervals or underlying sinus variability/sick sinus. In addition, false detection of atrial tachycardia may occur in a subcutaneous device during ectopy and regular normal sinus rhythm. Therefore, what is needed is a method for improving detection of atrial tachyarrhythmia to reduce false detection in a medical device.

DETAILED DESCRIPTION

In the following description, references are made to illustrative embodiments for carrying out the methods described herein. It is understood that other embodiments may be utilized without departing from the scope of the disclosure.

In various embodiments, ventricular signals are used for determining successive ventricular cycle lengths for use in detecting atrial arrhythmias. The atrial arrhythmia detection methods do not require an electrode positioned within the atrium as an atrial signal source to directly sense the atrial signal within the heart; i.e., the device may be a single chamber device having an electrode positioned only within the ventricle, or a subcutaneous device having no electrode positioned within the heart. The methods presented herein may be embodied in software, hardware or firmware in implantable or external medical devices. Such devices include implantable monitoring devices having cardiac EGM/ECG monitoring capabilities and associated EGM/ECG sense electrodes, which may be intracardiac, epicardial, or subcutaneous electrodes.

The methods described herein can also be incorporated in implantable medical devices having therapy delivery capabilities, such as single chamber or bi-ventricular pacing systems or ICDs that sense the R-waves in the ventricles and deliver an electrical stimulation therapy to the ventricles. The atrial arrhythmia detection methods presently disclosed may also be incorporated in external monitors having ECG electrodes coupled to the patient's skin to detect R-waves, e.g. Holter monitors, or within computerized systems that analyze pre-recorded ECG or EGM data. Embodiments may further be implemented in a patient monitoring system, such as a centralized computer system which processes data sent to it by implantable or wearable monitoring devices, including subcutaneous devices having loop recorders.

Figure 1:
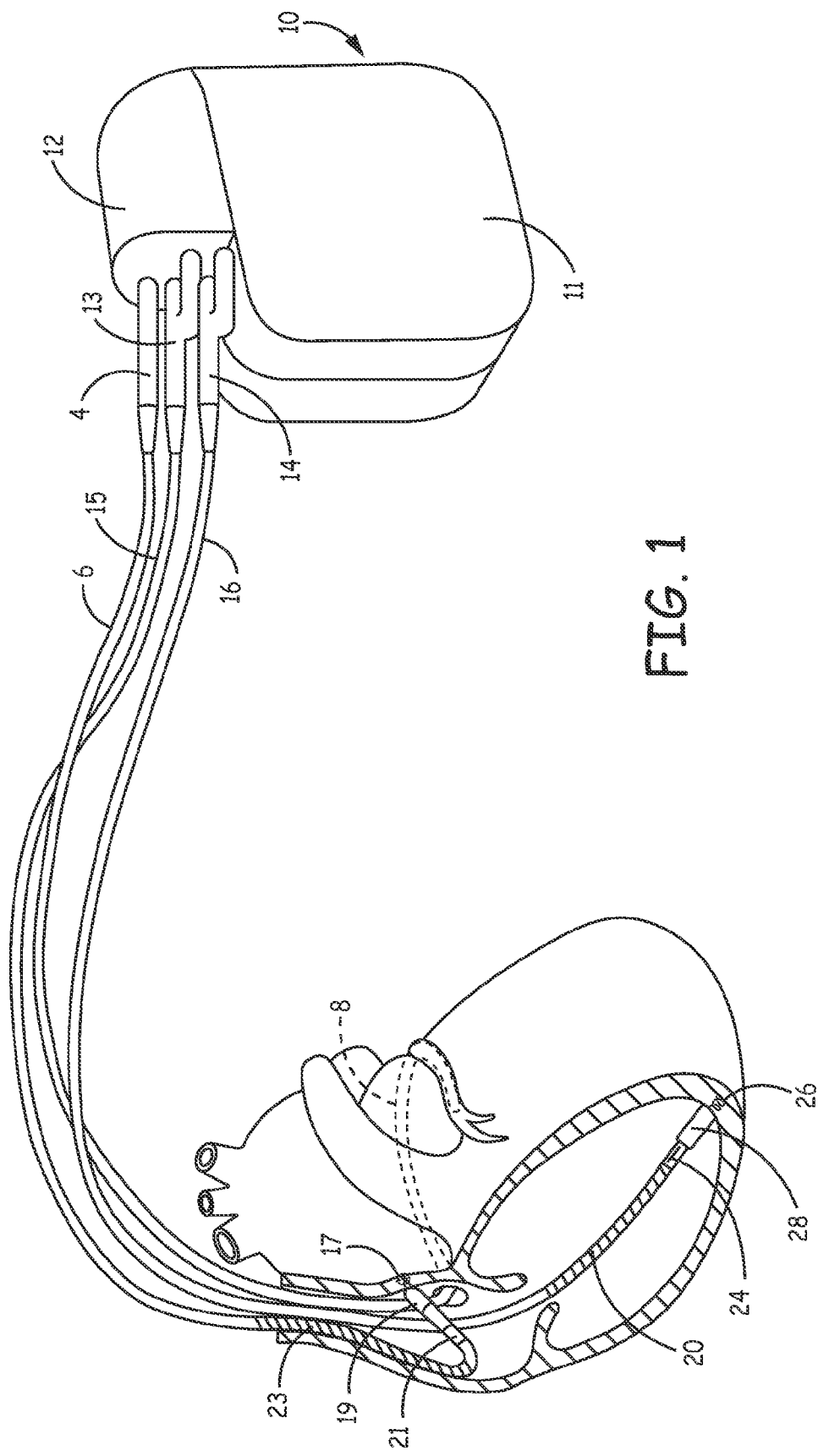
FIG. 1 is a schematic diagram of an exemplary medical device for detecting an arrhythmia according to an embodiment of the present disclosure.

FIG. 1 is a schematic diagram of an exemplary medical device for detecting an arrhythmia according to an embodiment of the present disclosure. As illustrated in FIG. 1, a medical device according to an embodiment of the present disclosure may be in the form of an implantable cardioverter defibrillator (ICD) 10 a connector block 12 that receives the proximal ends of a right ventricular lead 16, a right atrial lead 15 and a coronary sinus lead 6, used for positioning electrodes for sensing and stimulation in three or four heart chambers. Right ventricular lead 16 is positioned such that its distal end is in the right ventricle for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and a coil electrode 20, each of which are connected to an insulated conductor within the body of lead 16. The proximal end of the insulated conductors are coupled to corresponding connectors carried by bifurcated connector 14 at the proximal end of lead 16 for providing electrical connection to the ICD 10. It is understood that although the device illustrated in FIG. 1 is a dual chamber device, other devices such as single chamber devices may be utilized to perform the technique of the present disclosure described herein.

The right atrial lead 15 is positioned such that its distal end is in the vicinity of the right atrium and the superior vena cava. Lead 15 is equipped with a ring electrode 21 and an extendable helix electrode 17, mounted retractably within electrode head 19, for sensing and pacing in the right atrium. Lead 15 is further equipped with a coil electrode 23 for delivering high-energy shock therapy. The ring electrode 21, the helix electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as true bipolar pairs, commonly referred to as a "tip-to-ring" configuration. Further, electrode 17 and coil electrode 20 or electrode 24 and coil electrode 23 may be used as integrated bipolar pairs, commonly referred to as a "tip-to-coil" configuration. In accordance with the invention, ICD 10 may, for example, adjust the electrode configuration from a tip-to-ring configuration, e.g., true bipolar sensing, to a tip-to-coil configuration, e.g., integrated bipolar sensing, upon detection of oversensing in order to reduce the likelihood of future oversensing. In other words, the electrode polarities can be reselected in response to detection of oversensing in an effort to reduce susceptibility of oversensing. In some cases, electrodes 17, 21, 24, and 26 may be used individually in a unipolar configuration with the device housing 11 serving as the indifferent electrode, commonly referred to as the "can" or "case" electrode.

The device housing 11 may also serve as a subcutaneous defibrillation electrode in combination with one or more of the defibrillation coil electrodes 8, 20 or 23 for defibrillation of the atria or ventricles. It is recognized that alternate lead systems may be substituted for the three lead system illustrated in FIG. 1. While a particular multi-chamber ICD and lead system is illustrated in FIG. 1, methodologies included in the present invention may adapted for use with any single chamber, dual chamber, or multi-chamber ICD or pacemaker system, subcutaneous implantable device, or other internal or external cardiac monitoring device.

ICD 10 may alternatively be configured as a subcutaneous device having sensing or pacing electrodes incorporated on the housing 11 of the device in which case transvenous leads are not required. A subcutaneous device may be coupled to a lead tunneled subcutaneously or submuscularly for delivering transthoracic pacing pulses and/or sensing ECG signals. An exemplary subcutaneous device is described in commonly assigned U.S. patent application Ser. Nos. 14/604,111 and 14/604,260, both incorporated herein by reference in their entireties. The techniques described herein can also be implemented in an external device, e.g. including patch electrodes and optionally another physiological sensor if desired, that can sense variable parameters as described herein.

Figure 2:
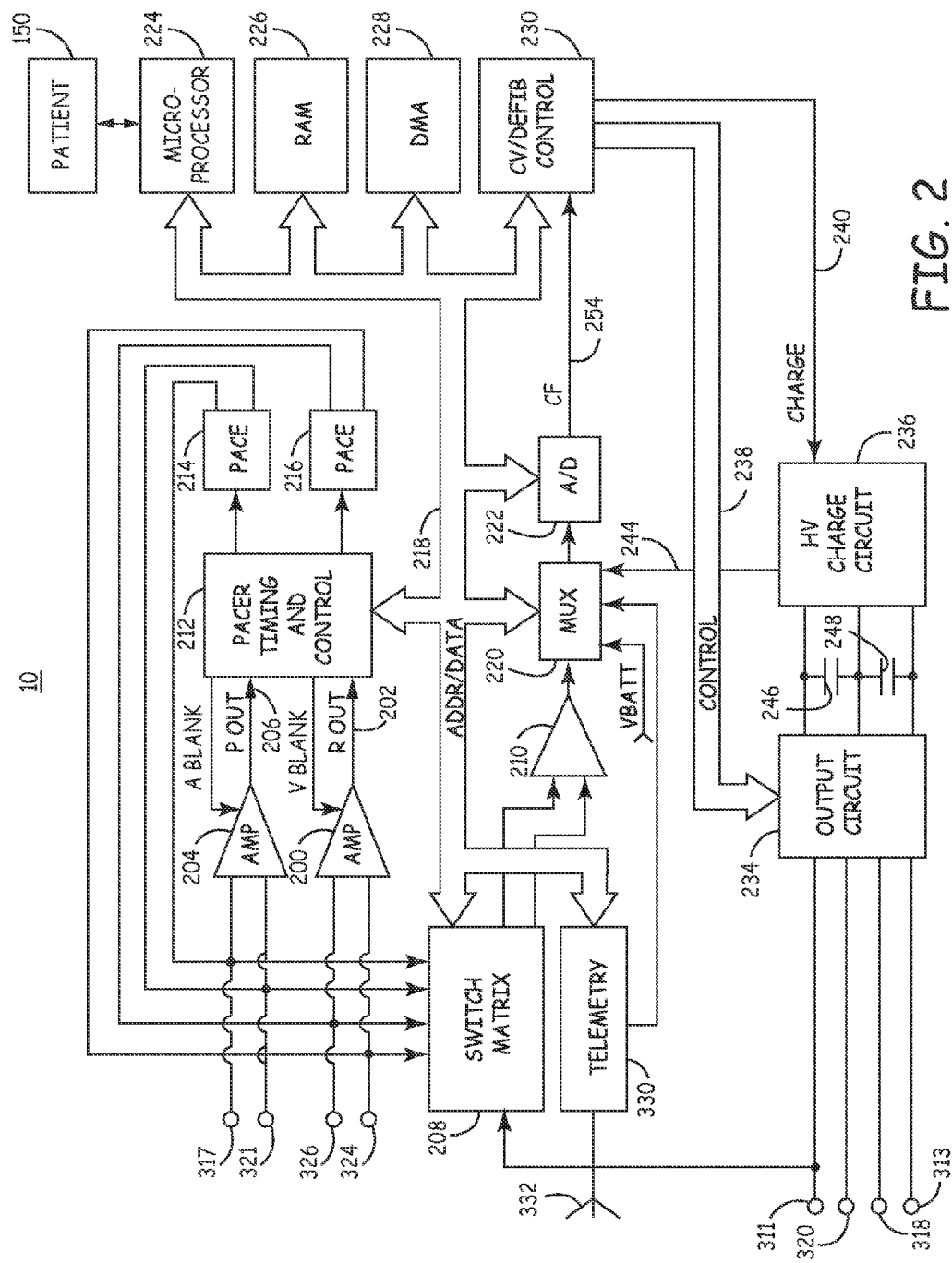
FIG. 2 is a functional schematic diagram of the medical device of FIG. 1.

FIG. 2 is a functional schematic diagram of the medical device of FIG. 1. This diagram should be taken as exemplary of the type of device with which the invention may be embodied and not as limiting. The disclosed embodiment shown in FIG. 2 is a microprocessor-controlled device, but the methods of the present invention may also be practiced with other types of devices such as those employing dedicated digital circuitry.

With regard to the electrode system illustrated in FIG. 1, ICD 10 is provided with a number of connection terminals for achieving electrical connection to the leads 6, 15, and 16 and their respective electrodes. A connection terminal 311 provides electrical connection to the housing 11 for use as the indifferent electrode during unipolar stimulation or sensing. The connection terminals 320, 313, and 318 provide electrical connection to coil electrodes 20, 8 and 23 respectively. Each of these connection terminals 311, 320, 313, and 318 are coupled to the high voltage output circuit 234 to facilitate the delivery of high energy shocking pulses to the heart using one or more of the coil electrodes 8, 20, and 23 and optionally the housing 11.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals. The atrial sense amplifier 204 and the ventricular sense amplifier 200 preferably take the form of automatic gain controlled amplifiers with adjustable sensitivity. In accordance with the invention, ICD 10 and, more specifically, microprocessor 224 automatically adjusts the sensitivity of atrial sense amplifier 204, ventricular sense amplifier 200 or both in response to detection of oversensing in order to reduce the likelihood of oversensing. Ventricular sense amplifier 200 and atrial sense amplifier 204 operate in accordance with originally programmed sensing parameters for a plurality of cardiac cycles, and upon detecting oversensing, automatically provides the corrective action to avoid future oversensing. In this manner, the adjustments provided by ICD 10 to amplifiers 200 and 204 to avoid future oversensing are dynamic in nature. Particularly, microprocessor 224 increases a sensitivity value of the amplifiers, thus reducing the sensitivity, when oversensing is detected. Atrial sense amplifier 204 and ventricular sense amplifier 200 receive timing information from pacer timing and control circuitry 212.

Specifically, atrial sense amplifier 204 and ventricular sense amplifier 200 receive blanking period input, e.g., ABLANK and VBLANK, respectively, which indicates the amount of time the electrodes are "turned off" in order to prevent saturation due to an applied pacing pulse or defibrillation shock. As will be described, the blanking periods of atrial sense amplifier 204 and ventricular sense amplifier 200 and, in turn, the blanking periods of sensing electrodes associated with the respective amplifiers may be automatically adjusted by ICD 10 to reduce the likelihood of oversensing. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensitivity, a signal is generated on the P-out signal line 206. Whenever a signal received by the ventricular sense amplifier 200 exceeds a ventricular sensitivity, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Specifically, microprocessor 224 may modify the electrode configurations based on detection of oversensing due to cardiac or non-cardiac origins. Upon detection of R-wave oversensing, for example, microprocessor 224 may modify the electrode configuration of the right ventricle from true bipolar sensing, e.g., tip-to-ring, to integrated bipolar sensing, e.g., tip-to-coil.

Signals from the electrodes selected for coupling to bandpass amplifier 210 are provided to multiplexer 220, and thereafter converted to multi-bit digital signals by A/D converter 222, for storage in random access memory 226 under control of direct memory access circuit 228 via data/address bus 218. Microprocessor 224 may employ digital signal analysis techniques to characterize the digitized signals stored in random access memory 226 to recognize and classify the patient's heart rhythm employing any of the numerous signal processing methodologies known in the art. An exemplary tachyarrhythmia recognition system is described in U.S. Pat. No. 5,545,186 issued to Olson et al, incorporated herein by reference in its entirety.

Upon detection of an arrhythmia, an episode of EGM data, along with sensed intervals and corresponding annotations of sensed events, are preferably stored in random access memory 226. The EGM signals stored may be sensed from programmed near-field and/or far-field sensing electrode pairs. Typically, a near-field sensing electrode pair includes a tip electrode and a ring electrode located in the atrium or the ventricle, such as electrodes 17 and 21 or electrodes 26 and 24. A far-field sensing electrode pair includes electrodes spaced further apart such as any of: the defibrillation coil electrodes 8, 20 or 23 with housing 11; a tip electrode 17 or 26 with housing 11; a tip electrode 17 or 26 with a defibrillation coil electrode 20 or 23; or atrial tip electrode 17 with ventricular ring electrode 24. The use of near-field and far-field EGM sensing of arrhythmia episodes is described in U.S. Pat. No. 5,193,535, issued to Bardy, incorporated herein by reference in its entirety. Annotation of sensed events, which may be displayed and stored with EGM data, is described in U.S. Pat. No. 4,374,382 issued to Markowitz, incorporated herein by reference in its entirety.

The telemetry circuit 330 receives downlink telemetry from and sends uplink telemetry to an external programmer, as is conventional in implantable anti-arrhythmia devices, by means of an antenna 332. Data to be uplinked to the programmer and control signals for the telemetry circuit are provided by microprocessor 224 via address/data bus 218. EGM data that has been stored upon arrhythmia detection or as triggered by other monitoring algorithms may be uplinked to an external programmer using telemetry circuit 330. Received telemetry is provided to microprocessor 224 via multiplexer 220. Numerous types of telemetry systems known in the art for use in implantable devices may be used.

The remainder of the circuitry illustrated in FIG. 2 is an exemplary embodiment of circuitry dedicated to providing cardiac pacing, cardioversion and defibrillation therapies. The pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

The microprocessor 224 includes associated read-only memory (ROM) in which stored programs controlling the operation of the microprocessor 224 reside. A portion of the random access memory (RAM) 226 may be configured as a number of recirculating buffers capable of holding a series of measured intervals for analysis by the microprocessor 224 for predicting or diagnosing an arrhythmia. In response to the detection of tachycardia, anti-tachycardia pacing therapy can be delivered by loading a regimen from microprocessor 224 into the pacer timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244, which is passed through the multiplexer 220. When the voltage reaches a predetermined value set by microprocessor 224, a logic signal is generated on the capacitor full (CF) line 254, terminating charging. The defibrillation or cardioversion pulse is delivered to the heart under the control of the pacer timing and control circuitry 212 by an output circuit 234 via a control bus 238. The output circuit 234 determines the electrodes used for delivering the cardioversion or defibrillation pulse and the pulse wave shape.

In one embodiment, the ICD 10 may be equipped with a patient notification system 150. Any patient notification method known in the art may be used such as generating perceivable twitch stimulation or an audible sound. A patient notification system may include an audio transducer that emits audible sounds including voiced statements or musical tones stored in analog memory and correlated to a programming or interrogation operating algorithm or to a warning trigger event as generally described in U.S. Pat. No. 6,067,473 issued to Greeninger et al., incorporated herein by reference in its entirety.

Figure 3:
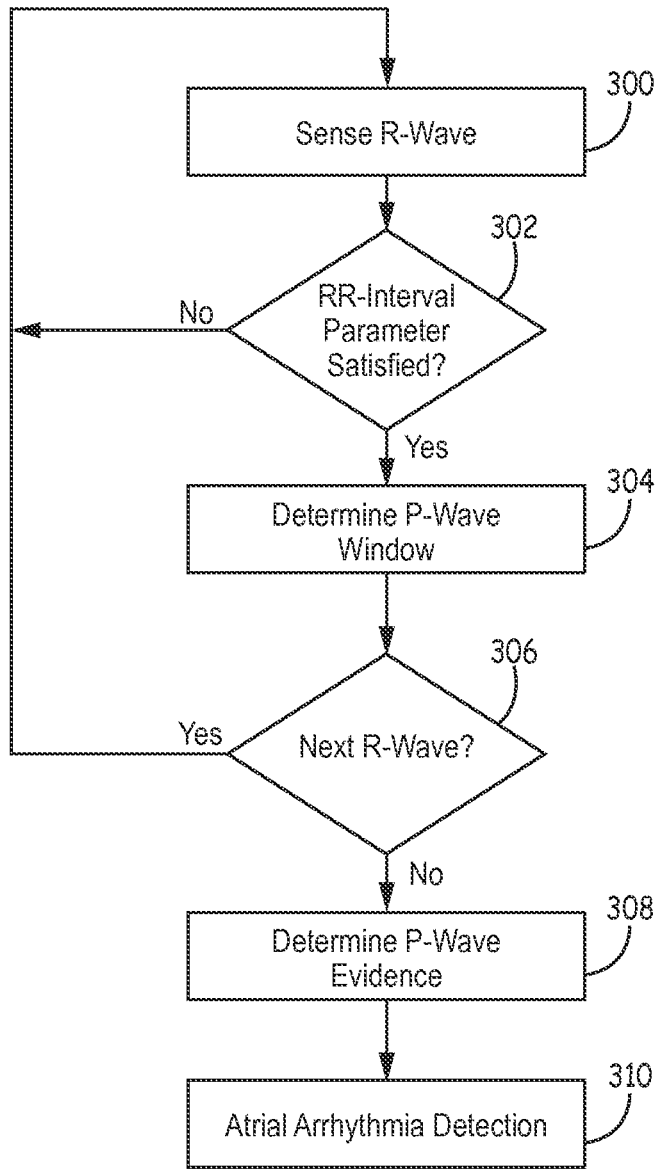
FIG. 3 is a flowchart of a method for detecting an atrial arrhythmia according to an embodiment of the disclosure.

FIG. 3 is a flowchart of a method for detecting an atrial arrhythmia according to an embodiment of the disclosure. As illustrated in FIG. 3, in order to determine whether a sensed cardiac signal is an atrial tachycardia event, the device determines whether the cardiac signal contains a P-wave portion, the results of which are utilized to augment an atrial tachycardia determination process. For example, the determination as to whether a P-wave is detected may be utilized to augment detection of atrial arrhythmias based on the irregularity of ventricular cycles having RR intervals that exhibit discriminatory signatures when plotted in a Lorenz scatter plot, such as is generally disclosed by Ritscher et al. in U.S. Pat. No. 7,031,765, or in U.S. Pat. No. 8,639,316 to Sarkar, both incorporated herein by reference in their entireties. Other atrial arrhythmia determination methods are generally disclosed by Sarkar, et al. in U.S. Pat. No. 7,623,911 and in U.S. Pat. No. 7,537,569, and by Houben in U.S. Pat. No. 7,627,368, all of which patents are also incorporated herein by reference in their entireties.

According to one embodiment, for example, during determination of signal characteristics for augmenting atrial tachycardia detection, the device senses the cardiac signal and identifies R-waves in response to the sensed cardiac signal using any known cardiac signal sensing and detection scheme, such as that disclosed in U.S. Pat. No. 5,117,824, by Keimel, et al., for example, described above and incorporated herein by reference in its entirety. Upon detection of an R-wave associated with the sensed cardiac signal, Block 300, the device determines whether the R-wave satisfies one or more RR-interval parameters, Block 302, described below. If the RR-interval parameter or parameters are not satisfied, No in Block 302, the device waits for the next sensed R-wave, Block 300 and the process Block 300-302 is repeated using the next R-wave. If the RR-interval parameter or parameters are satisfied, Yes in Block 302, the device determines a P-wave window associated with the R-wave, Block 304, as described below.

Upon determination of the P-wave window, the device determines whether a predetermined number of R-waves have been identified, Block 306. The predetermined number of R-waves required to satisfy the determination in Block 306 may be set as one or more R-waves, and according to one embodiment is set as four R-waves for example. If the predetermined number of R-waves have not been identified and therefore a next R-wave is needed, Yes in Block 306, the device waits for the next sensed R-wave, Block 300 and the process Block 300-306 is repeated using the next R-wave. If the predetermined number of R-waves have been identified and therefore a next R-wave is not needed, No in Block 306, the device determines P-wave evidence, Block 308, described below, and utilizes the determined P-wave evidence to augment atrial arrhythmia detection, Block 310, as described, for example, in commonly assigned U.S. patent application Ser. No. 14/695,111, incorporated herein by reference in it's entirety.

Figure 4:
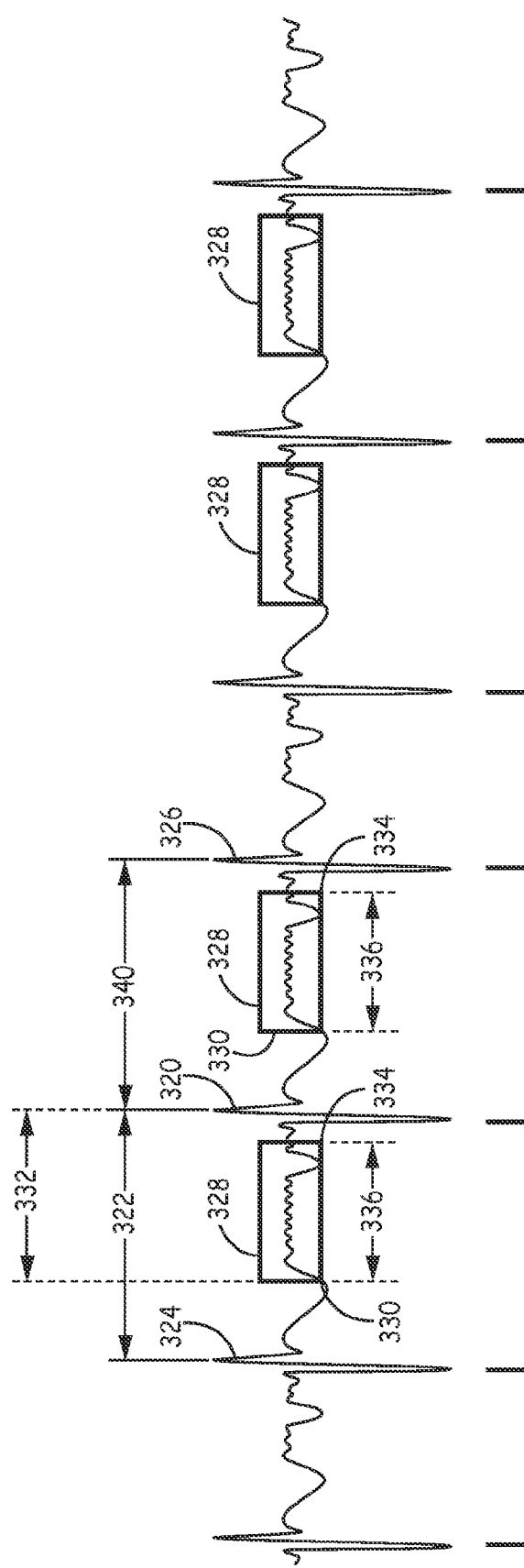
FIG. 4 is a schematic diagram of detecting an atrial arrhythmia according to an embodiment of the disclosure.

FIG. 4 is a schematic diagram of detecting an atrial arrhythmia according to an embodiment of the disclosure. As illustrated in FIGS. 3 and 4, in order to determine whether a sensed R-wave 320 satisfies the RR-interval parameters in Block 302, the device determines whether an RR interval 322 extending between the current R-wave 320 and a previous sensed R-wave 324 is greater than an interval threshold, such as 780 ms for example. If the RR interval 322 is not greater than the interval threshold, the RR-interval parameter is not satisfied, No in Block 302, and the process is repeated with the next RR interval 326. If the RR interval 322 is greater than the interval threshold, the RR interval parameter is satisfied, Yes in Block 302.

According to another embodiment, additional RR interval parameters may also be included in the determination as to whether the RR interval parameters have been satisfied in Block 302. For example, using R wave 326 as an example, in addition to the determination of whether the associated RR interval 340 satisfies the RR interval threshold, the device may also compare the RR interval 340 associated with the current R wave 326 with one or more previously determined RR intervals, such as interval 322 for example, and determine whether a relative change associated with the current RR-interval 340 is greater than a change threshold, such as 100 ms, for example. If the relative change associated with the current RR-interval is not greater than the change threshold, the RR interval parameter is not satisfied in Block 302. If the relative change associated with the current RR interval is greater than the change threshold, the RR-interval parameter is satisfied in Block 302.

In this way, if one of the RR intervals parameters are not satisfied, no P-wave window determination is made, and the process is repeated with the next R wave. If the RR interval parameter or one of the RR interval parameters are satisfied, the RR interval parameter is satisfied in Block 302, and the device determines a P wave window 328 associated with the R-wave 320 for determining whether the R wave 320 includes an associated P-wave. For example, in order to determine the P wave window 328, the device determines a P-wave window start point 330 located a predetermined distance 332 prior to the R-wave, such as 620 ms for example, and a P wave window endpoint 334 is located at a predetermined distance 336 subsequent to the P wave start point 330, such as 600 ms, for example, so that the P wave window 328 extends 600 ms between the P wave start point 330 and the P wave endpoint 334. Each time a P wave window 328 is determined, a P wave counter is updated by one, until the predetermined number of P wave windows are identified, such as four P wave windows, for example.

Figure 5:
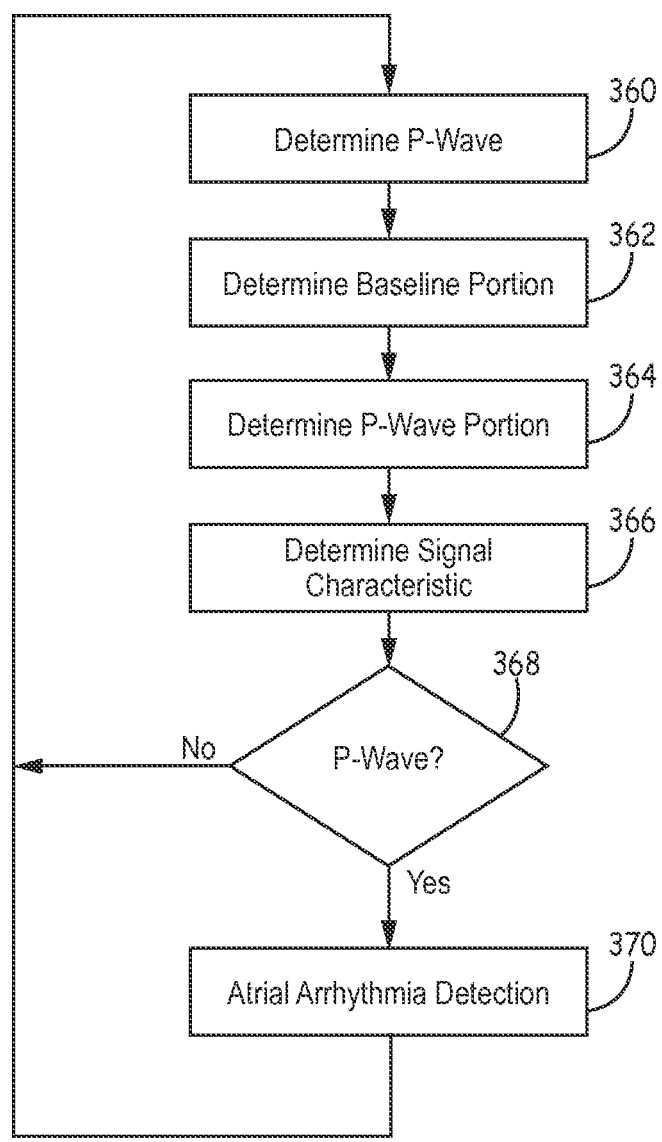
FIG. 5 is a flowchart of a method of detecting an atrial arrhythmia in a medical device according to an embodiment of the disclosure.

FIG. 5 is a flowchart of a method of detecting an atrial arrhythmia in a medical device according to an embodiment of the disclosure. In response to the predetermined number of P-waves being identified, No in Block 306 of FIG. 3, the device determines P-wave evidence for determining whether a P-wave is likely detected, Block 308, and utilizes the determined P-wave evidence to augment atrial arrhythmia detection, Block 310, described, for example, in commonly assigned U.S. patent application Ser. No. 14/695,111, incorporated herein by reference in it's entirety. As illustrated in FIG. 5, during the determination of P-wave evidence, the device determines a characteristic P-wave in response to the current determined P-waves, Block 360. For example, according to one embodiment, the device determines an average P-wave from the four determined P-waves that is identified as the characteristic P-wave. The associated P-wave window is then divided into a baseline portion, Block 362, and a P-wave portion, Block 364, and determines signal characteristics, Block 366, for one or both of the baseline window and the P-wave window. A determination is then made, based on the determined signal characteristics, whether the characteristic P-wave is confirmed as being a P-wave, Block 368.

If the characteristic P-wave is not confirmed as being a P-wave, No in Block 368, the device waits for the next predetermined number of P-waves to be identified, Yes in Block 306 of FIG. 3, and the process, Blocks 360-368, is repeated using the next identified P-waves. If the characteristic P-wave is confirmed as being a P-wave, Yes in Block 368, the device utilizes the determination of a P-wave being present to augment atrial arrhythmia detection, Block 370, as described for example, in commonly assigned U.S. patent application Ser. No. 14/695,111, incorporated herein by reference in it's entirety.

Figure 6:
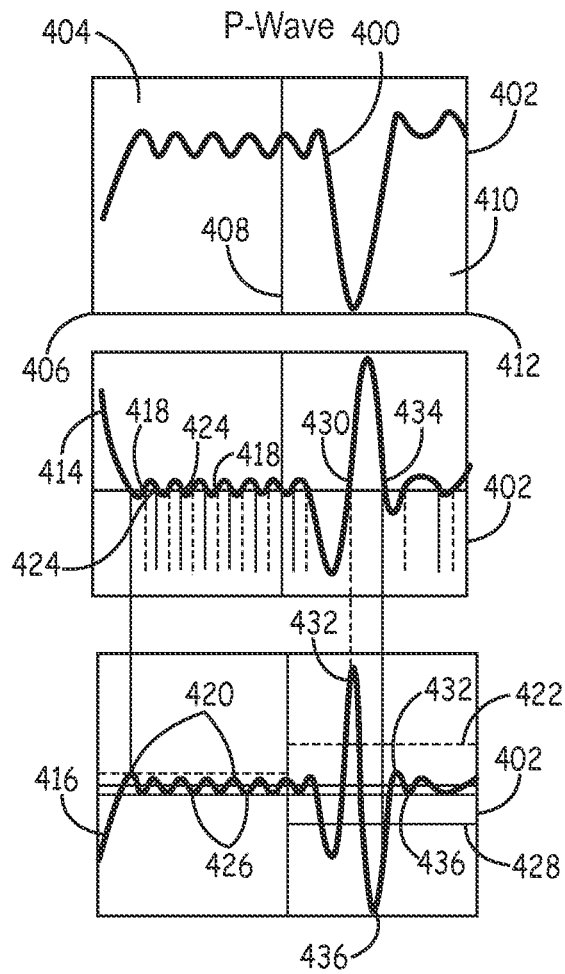
FIG. 6 is a schematic diagram of detecting an atrial arrhythmia in a medical device, according to an embodiment of the disclosure.

FIG. 6 is a schematic diagram of detecting an atrial arrhythmia in a medical device, according to an embodiment of the disclosure. As illustrated in FIGS. 5 and 6, in order to determine P-wave evidence (Block 308 of FIG. 3), the device determines a characteristic P-wave 400 having a characteristic P wave window 402 determined by averaging the determined four P-wave windows, as described above. The device divides the P-wave window 402 into a baseline portion 404, extending from the P-wave window start point 406 to a midpoint of the window 408, and a P-wave portion 410, extending from the midpoint of the window 408 to a P-wave window endpoint 412. The device determines a first derivative of the P-wave signal 414 and a second derivative of the p-wave signal 416, and determines corresponding second derivative values 420 associated with positive going zero crossings 418 of the first derivative signal 414 within the baseline portion 404 of the first derivative signal window 402. In one embodiment, the first derivative of the P wave signal can be computed as the difference between points separated by eight samples, and the second derivative can be computed as the difference between points separated by four sample in the first derivative.

The device determines the maximum amplitude of the second derivative values 420 associated with the positive going zero crossings 418, and the determined maximum amplitude value is then used to generate a first threshold 422 for evaluating the second derivative P-wave signal 416 within the P-wave portion 410 of the second derivative window 402. According to one embodiment, the threshold 422 is set as a multiple of the maximum of the second derivative values 420, such as twice the maximum of the second derivative values 420, for example.

In the same way, the device determines a corresponding second derivative value 426 for each negative going zero crossing 424 of the derivative signal 414 within the baseline portion 404 of the window 402. A minimum amplitude of the second derivative values 426 associated with the negative going first derivative zero crossings 424 is determined, and the determined minimum amplitude value is used to generate a second threshold 428 for evaluating the second derivative P-wave signal 416 within the P-wave portion 410 of the window 402. According to one embodiment, the threshold 428 is set as a multiple of the minimum of the second derivative values 426, such as twice the minimum of the second derivative values 426, for example.

Using the first threshold 422 determined in response to the determined maximum of the second derivative values 420, the device determines, for each positive going zero crossing 430 of the first derivative signal within the P-wave portion 410 of the first derivative window, a corresponding amplitude 432 of the second derivative signal within the P-wave portion 410 of the corresponding second derivative signal 416. The device compares the resulting maximum amplitudes 432 of the second derivative signal 416 signal within the P-wave portion 410 of the window 402 to the first threshold 422. Similarly, using the second threshold 422 determined in response to the determined minimum of the second derivative values 420, the device compares, for one or more negative going zero crossing 434 of the first derivative signal 414, the corresponding minimum amplitude 436 of the second derivative signal 416 signal within the P-wave portion 410 of the window 402 to the second threshold 428.

A P-wave is determined to have occurred, Yes in Block 368 of FIG. 5, if either the number of maximum amplitudes 432 determined to be greater than or equal to the first threshold 422 is equal to one, or the number of minimum amplitudes 432 determined to be less than or equal to the second threshold 428 is equal to one. If both the number of maximum amplitudes 432 determined to be greater than or equal to the first threshold 422 and the number of minimum amplitudes 432 determined to be less than or equal to the second threshold 428 is not equal to one, a P-wave is not determined to have occurred, No in Block 368 of FIG. 5. The result of the determination of whether a P-wave is identified is then used during the determination of an atrial arrhythmia event, as described for example, in commonly assigned U.S. patent application Ser. No. 14/695,111, incorporated herein by reference in it's entirety.

Thus, an apparatus and method have been presented in the foregoing description with reference to specific embodiments. It is appreciated that various modifications to the referenced embodiments may be made without departing from the scope of the invention as set forth in the following claims.

The invention claimed is:

1. A method of determining a P-wave of a cardiac signal in an implantable medical device, comprising:
   sensing the cardiac signal;
   identifying one or more R-waves within the cardiac signal;
   determining one or more P-wave sensing windows, wherein each of the P-wave sensing window is associated with one of the one or more identified R-waves;
   determining a characteristic P-wave sensing window based on the one or more determined P-wave sensing windows, the characteristic P-wave sensing window having a first portion and a second portion;
   determining a first derivative signal of the cardiac signal within the characteristic P-wave sensing window;
   determining a second derivative signal of the cardiac signal within the characteristic P-wave sensing window;
   analyzing the first derivative and the second derivative of the cardiac signal within the characteristic P-wave window to determine a first set of signal characteristics of the cardiac signal within the first portion of the characteristic P-wave sensing window and a second set of signal characteristics of the cardiac signal within the second portion of the characteristic P-wave sensing window, the signal characteristics including zero crossings of the first derivative signal and amplitudes of the second derivative signal corresponding to the determined zero crossings; and detecting the P-wave based on the first and the second set of signal characteristics.

2. The method of claim 1, further comprising:
determining a maximum amplitude of the determined amplitudes of the second derivative signal within the first portion; and
comparing the amplitudes of the second derivative signal within the second portion to an amplitude threshold, wherein the amplitude threshold is determined based on the determined maximum amplitude of the second derivative signal within the first portion.

3. The method of claim 2, wherein the amplitude threshold comprises a multiple of the determined maximum amplitude of the second derivative signal within the first portion.

4. The method of claim 2, further comprising:
determining a number of times the determined amplitudes of the second derivative signal within the second portion are greater than the amplitude threshold; and
determining the P-wave based on the determined number of times.

5. The method of claim 4, further comprising:
determining an RR-interval associated with one of the one or more determined R-wave;
determining a relative change associated with the RR-interval;
comparing the determined RR-interval to an interval threshold and the determined relative change to a change threshold; and
confirming the determined R-wave, wherein the P-wave sensing window is determined in response to the confirmed R-wave.

6. The method of claim 1, further comprising:
determining a maximum amplitude of the determined amplitudes of the second derivative signal within the first portion;
determining a maximum amplitude threshold based on the determined maximum amplitude of the second derivative signal within the first portion;
determining a minimum amplitude of the determined amplitudes of the second derivative signal within the first portion;
determining a minimum amplitude threshold based on the determined minimum amplitude of the second derivative signal within the first portion; and
comparing the amplitudes of the second derivative signal within the second portion to the maximum amplitude threshold and the minimum amplitude threshold.

7. The method of claim 6, further comprising:
determining a first number of times the determined amplitudes of the second derivative signal within the second portion are greater than the maximum amplitude threshold;
determining a second number of times the determined amplitudes of the second derivative signal within the second portion are less than the minimum amplitude threshold; and
determining the P-wave based on both the determined first number of times and the determined second number of times.

8. The method of claim 7, further comprising determining the sensed cardiac signal within the first portion and within the second portion as a P-wave in response to either the first number of times being equal to one or the second number of times being equal to one.

9. The method of claim 1, wherein the medical device comprises a subcutaneous device.

10. An implantable medical device for determining a P-wave in a cardiac signal, comprising:
a plurality of electrodes configured to sense the cardiac signal; and
a processor configured to identify one or more R-waves within the cardiac signal, determine one or more P-wave sensing windows, wherein each of the P-wave sensing windows is associated with one of the one or more identified R-waves, determine a characteristic P-wave sensing window based on the one or more determined P-wave sensing windows, the characteristic P-wave sensing window having a first portion and a second portion, determine a first derivative signal of the cardiac signal within the characteristic P-wave sensing window, determine a second derivative signal of the cardiac signal within the characteristic P-wave sensing window, analyze the first derivative and the second derivative of the cardiac signal within the characteristic P-wave window to determine a first set of signal characteristics of the cardiac signal within the first portion of the characteristic P-wave sensing window and a second set of signal characteristics of the cardiac signal within the second portion of the characteristic P-wave sensing window, the signal characteristics including zero crossings of the first derivative signal and amplitudes of the second derivative signal corresponding to the determined zero crossings, and detect the P-wave based on the first and the second set of signal characteristics.

11. The medical device of claim 10, wherein the processor is further configured to determine a maximum amplitude of the determined amplitudes of the second derivative signal within the first portion, and compare the amplitudes of the second derivative signal within the first portion, and compare the amplitudes of the second derivative signal within the second portion to an amplitude threshold, wherein the amplitude threshold is determined based on the determined maximum amplitude of the second derivative signal within the first portion.

12. The medical device of claim 11, wherein the amplitude threshold comprises a multiple of the maximum amplitude of the second derivative signal within the first portion.

13. The medical device of claim 11, wherein the processor is configured to determine a number of times the determined amplitudes of the second derivative signal within the second portion are greater than the amplitude threshold, and determine the P-wave based on the determined number of times.

14. The medical device of claim 13, wherein the processor is configured to determine an RR-interval associated with one of the one or more determined R-waves, determine a relative change associated with the RR-interval, compare the determined RR-interval to an interval threshold and the determined relative change to a change threshold, and confirming the determined R-wave, wherein the P-wave sensing window is determined in response to the confirmed R-wave.

15. The medical device of claim 10, wherein the processor is configured to determine a maximum amplitude of the determined amplitudes of the second derivative signal within the first portion, determine a maximum amplitude threshold based on the determined maximum amplitude of the second derivative signal within the first portion, determine a minimum amplitude of the determined amplitudes of the second derivative signal within the first portion, determine a minimum amplitude threshold based on the determined minimum amplitude of the second derivative signal within the first portion, and compare the amplitudes of the second derivative signal within the second portion to the maximum amplitude threshold and the minimum amplitude threshold.

16. The medical device of claim 15, wherein the processor is configured to determine a first number of times the determined amplitudes of the second derivative signal within the second portion are greater than the maximum amplitude threshold, determine a second number of times the determined amplitudes of the second derivative signal within the second portion are less than the minimum amplitude threshold, and determine the P-wave based on both the determined first number of times and the determined second number of times.

17. The medical device of claim 16, wherein the processor is configured to determine the sensed cardiac signal within the first portion and within the second portion as a P-wave in response to either the first number of times being equal to one or the second number of times being equal to one.

18. The medical device of claim 10, wherein the medical device comprises a subcutaneous device.

19. The medical device of claim 10, wherein the processor is further configured to determine a maximum amplitude of the determined amplitudes of the second derivative of the cardiac signal corresponding to positive going zero crossings within the first portion of the characteristic P-wave sensing window, set a positive amplitude threshold based on the determined maximum amplitude, compare the amplitudes of the second derivative of the cardiac signal corresponding to positive going zero crossings within the second portion of the characteristic P-wave sensing window to the positive amplitude threshold, and detecting the P-wave based at least on the comparisons to the positive amplitude threshold.

20. The medical device of any one of claims 19, wherein the processor is configured to determine a first number of times the amplitudes of the second derivative of the cardiac signal corresponding to positive going zero crossings within the second portion of the characteristic P-wave sensing window are greater than or equal to the positive amplitude threshold and detect the P-wave when the first number of times is equal to one.

21. The medical device of claim 20, wherein the processor is further configured to determine a minimum amplitude of the determined amplitudes of the second derivative of the cardiac signal corresponding to negative going zero crossings within the first portion of the characteristic P-wave sensing window, set a negative amplitude threshold based on the determined minimum amplitude, compare the amplitudes of the second derivative of the cardiac signal corresponding to negative going zero crossings within the second portion of the characteristic P-wave sensing window to the negative amplitude threshold, and detecting the P-wave based on at least the comparisons to the negative amplitude threshold.

22. The medical device of claim 21, wherein the processor is configured to determine a second number of times the amplitudes of the second derivative of the cardiac signal corresponding to negative going zero crossings within the second portion of the characteristic P-wave sensing window are less than or equal to the negative amplitude threshold and detect the P-wave when the second number of times is equal to one.

23. The medical device of claim 21, wherein the processor is configured to determine that no P-wave occurred within the characteristic P-wave sensing window when both the first number of times is not equal to one and the second number of times is not equal to one.

24. The medical device of claim 10, wherein the processor determines the characteristic P-wave window by averaging the cardiac signal of the one or more determined P-wave sensing windows.

25. The medical device of claim 10, wherein the processor is configured to determine RR-intervals associated with each of the one or more identified R-waves, determine whether each of the determined RR-intervals satisfy one or more RR-interval parameters, and determine the one or more P-wave sensing windows only for the R-waves having associated RR-interval that satisfy the one or more RR-interval parameters.

26. The medical device of claim 25, wherein the one or more RR-interval parameters include at least an interval length parameter and RR-intervals satisfy the interval length parameter when the RR-interval is greater than an interval threshold.

27. The medical device of claim 25, wherein the one or more RR-interval parameters includes at least a relative change parameter and RR-intervals satisfy the relative change parameters when RR-intervals that have changed by more than a relative change threshold compared to a previous RR-interval.

28. The medical device of claim 10, wherein the first portion of the characteristic P-wave sensing window is a baseline portion and the second portion of the characteristic P-wave sensing window is a P-wave portion.

29. The medical device of claim 10, further comprising augmenting atrial arrhythmia detection based on the determination of the P-wave being present.

30. A non-transitory computer-readable medium storing a set of instructions which cause a processor of an implantable medical device to perform a method of determining a P-wave of a cardiac signal, comprising:
  sensing the cardiac signal;
  identifying one or more R-waves within the cardiac signal;
  determining one or more P-wave sensing windows, wherein each of the P-wave sensing window is associated with one of the one or more identified R-waves;
  determining a characteristic P-wave sensing window based on the one or more determined P-wave sensing windows, the characteristic P-wave sensing window having a first portion and a second portion;
  determining a first derivative signal of the cardiac signal within the characteristic P-wave sensing window;
  determining a second derivative signal of the cardiac signal within the characteristic P-wave sensing window;
  analyzing the first derivative and the second derivative of the cardiac signal within the characteristic P-wave window to determine a first set of signal characteristics of the cardiac signal within the first portion of the characteristic P-wave sensing window and a second set of signal characteristics of the cardiac signal within the second portion of the characteristic P-wave sensing window, the signal characteristics including zero crossings of the first derivative signal and amplitudes of the second derivative signal corresponding to the determined zero crossings; and
  detecting the P-wave based on the first and the second set of signal characteristics.

* * * * *